(12) United States Patent
Heider et al.

(10) Patent No.: US 6,372,441 B1
(45) Date of Patent: Apr. 16, 2002

(54) METHOD FOR DIAGNOSIS AND THERAPY OF HODGKIN'S LYMPHOMAS

(75) Inventors: Karl-Heinz Heider, Stockerau; Kurt Zatloukal; Christine Beham-Schmid, both of Graz, all of (AT)

(73) Assignees: Forschungszentrum Karlsruhe GmbH; Boehringer Ingelheim International GmbH, both of (DE)

(*) Notice: Subject to any disclaimer, the term of this patent is extended or adjusted under 35 U.S.C. 154(b) by 0 days.

(21) Appl. No.: 09/331,254
(22) PCT Filed: Dec. 17, 1997
(86) PCT No.: PCT/EP97/07081
 § 371 Date: Dec. 21, 1999
 § 102(e) Date: Dec. 21, 1999
(87) PCT Pub. No.: WO98/28625
 PCT Pub. Date: Jul. 2, 1998

(30) Foreign Application Priority Data

Dec. 20, 1996 (DE) .......................................... 196 53 607

(51) Int. Cl.[7] .............................................. G01N 33/53
(52) U.S. Cl. .......................... 435/7.1; 435/6; 435/7.23; 435/188; 530/387.3; 530/388.85
(58) Field of Search ................................ 435/7.1, 7.23, 435/6, 188, 7.24, 7.9; 530/387.1, 387.3, 388.8, 388.85, 391.3, 388.1, 388.7, 391.7, 391.9

(56) References Cited

FOREIGN PATENT DOCUMENTS

| EP | 0 531 300 B1 | 3/1993 |
| EP | 0 538 754 A2 | 4/1993 |
| WO | WO 94/02633 | 2/1994 |
| WO | WO 94/12631 | 6/1994 |
| WO | WO 95/00658 | 1/1995 |
| WO | WO 95/00851 | 1/1995 |

OTHER PUBLICATIONS

Savage et al., Br. J. Cancer 67:304–310, 1993.*
Chaudhary et al., Proc. Natl. Acad. Sci. USA 87:1066–1070, 1990.*
Seaver., Genetic Engineering news 14: pp. 10 and 21, 1994.*
Jian., Scientific american 271:58–65, 1994.*
Chatterjee et al., Cancer immunol. immunother. 38:75–82, 1994.*
Gura., Science 278:1041–1042, 1997.*
Breitz, H.B., et al., "Clinical Experience with Rhenium–186–Labeled Monoclonal Antibodies for Radioimmunotherapy: Results of Phase I Trials," *J. Nucl. Med.* 33:1099–1109 (May 1992).
Breitz, H.B., et al., "Pharmacokinetics and Normal Organ Dosimetry Following Intraperitoneal Rhenium–186–Labeled Monoclonal Antibody," *J. Nucl. Med.* 36:754–761 (May 1995).
Ermak, G., et al., "Restricted Patterns of CD44 Variant Exon Expression in Human Papillary Thyroid Carcinoma," *Cancer Res.* 56:1037–1042 (Mar. 1996).
Fox, S.B., et al., "CD44 and cancer screening," *Lancet* 342:548–549 (Aug. 1993).
Fox, S.B., et al., "Normal Human Tissues, in Addition to Some Tumors, Express Multiple Different CD44 Isoforms," *Cancer Res.* 54:4539–4546 (Aug. 1994).
Friedrichs, K., et al., "CD44 Isoforms Correlate with Cellular Differentiation but not with Prognosis in Human Breast Cancer," *Cancer Res.* 55:5424–5433 (Nov. 1995).
Fujiwara, K., et al., "Expression of a Lymphocyte Adhesion Molecule (CD44) in Malignant Lymphomas: Relevance to Primary Site, Histological Subtype and Clinical Stage," *Acta Med. Okayama* 47:215–222 (Jun. 1993).
Ghaffari, S., et al., "Differentiation–Associated Changes in CD44 Isoform Expression During Normal Hematopoiesis and Their Alteration in Chronic Myeloid Leukemia," *Blood* 86:2976–2985 (Oct. 1995).
Günthert, U., et al., A New Variant of Glycoprotein CD44 Confers Metastatic Potential to Rat Carcinoma Cells, *Cell* 65:13–24 (Apr. 1991).
Heider, K.–H., et al., "A Human Homologue of the Rat Metastasis–associated Variant of CD44 Is Expressed in Colorectal Carcinomas and Adenomatous Polyps," *J. Cell Biol.* 120:227–233 (Jan. 1993).
Heider, K.–H., et al., "Expression of CD44 isoforms in human renal cell carcinomas," *Virchows Arch.* 428:267–273 (Jul. 1996).
Hofmann, M., et al., "CD44 Splice Variants Confer Metastatic Behavior in Rats: Homologous Sequences Are Expressed in Human Tumor Cell Lines," *Cancer Res.* 51:5292–5297 (Oct. 1991).
Horst, E., et al., "Expression of a Human Homing Receptor (CD44) in Lymphoid Malignancies and Related Stages of Lymphoid Development," *Leukemia* 4:383–389 (May 1990).
Horst, E., et al., "Adhesion Molecules in the Prognosis of Diffuse Large–Cell Lymphoma: Expression of a Lymphocyte Homing Receptor (CD44), LFA–1 (CD11a/18), and ICAM–1 (CD54)," *Leukemia* 4:595–599 (Aug. 1990).

(List continued on next page.)

Primary Examiner—Sheela Huff
Assistant Examiner—Larry R. Helms
(74) *Attorney, Agent, or Firm*—Sterne, Kessler, Goldstein & Fox P.L.L.C.

(57) ABSTRACT

The invention relates to a method for diagnosing and treating Hodgkin's lymphomas (lymphogranulomatosis) which is based on the expression of the variant exon v10 of the CD44 gene as a molecular marker or target. There is a significant correlation between v10 expression and the stage and prognosis of the disease. In a preferred embodiment, v10-specific antibody molecules are used to measure the expression of the exon in samples. In another preferred embodiment, radiolabelled v10-specific antibodies are used to treat Hodgkin's lymphomas.

7 Claims, 3 Drawing Sheets

OTHER PUBLICATIONS

Figure 1A:
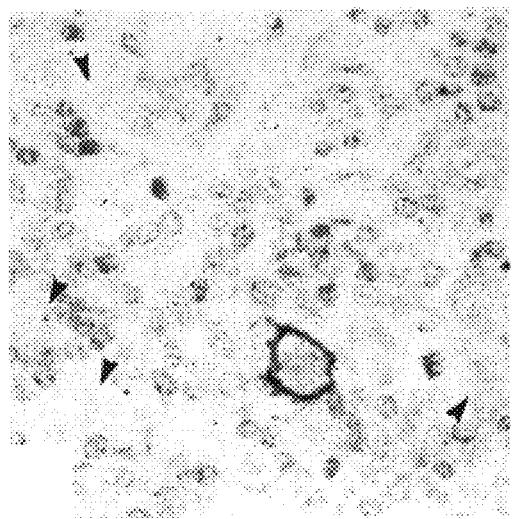

Jackson, D.G., et al., "Multiple Variants of the Human Lymphocyte Homing Receptor CD44 Generated by Insertions at a Single Site in the Extracellular Domain," *J. Biol. Chem. 267*:4732–4739 (Mar. 1992).

Jalkanen, S., et al., "Lymphocyte Homing and Clinical Behavior of Non–Hodgkin's Lymphoma," *J. Clin. Invest. 87*:1835–1840 (May 1991).

Juweid, M., et al., "Treatment of Non–Hodgkin's Lymphoma with Radiolabeled Murine, Chimeric, or Humanized LL2, an Anti–CD22 Monoclonal Antibody," *Cancer Res. (Suppl.) 55*:5899s–5907s (Dec. 1995).

Kaufmann, M., et al., "CD44 variant exon epitopes in primary breast cancer and length of survival," *Lancet 345*:615–619 (Mar. 1995).

Koopman, G., et al., "Activated Human Lymphocytes and Aggressive Non–Hodgkin's Lymphomas Express a Homologue of the Rat Metastasis–associated Variant of CD44," *J. Exp. Med. 177*:897–904 (Apr. 1993).

Mackay, C.R. et al., "Expression and Modulation of CD44 Variant Isoforms in Humans," *J. Cell. Biol. 124*:71–82 (Jan. 1994).

Möller, P., et al., "Venular endothelium binding molecules CD44 and LECAM–1 in normal and malignant B–cell populations. A comparative study," *Virchows Arch. A. Pathol. Anat. 421*:305–313 (Jul. 1992).

Mulder, J.–W.R., et al., "Colorectal cancer prognosis and expression of exon–v6–containing CD44 proteins," *Lancet 344*:1470–1472 (Nov. 1994).

Pals, S.T., et al., "Expression of Lymphocyte Homing Receptor as a Mechanism of Dissemination in Non–Hodgkin's Lymphoma," *Blood 73*:885–888 (Mar. 1989).

Picker, L.J., et al., "Expression of Lymphocyte Homing Receptor Antigen in Non–Hodgkin's Lymphoma," *Am. J. Pathol. 130*:496–504 (Mar. 1988).

Press, O. W., et al., "Phase II trial of $^{131}$I–B1 (anti–CD20) antibody therapy with autologous stem cell transplantation for relapsed B cell lymphomas," *Lancet 346*:336–340 (Aug. 1995).

Quadri, S.M., et al., "Evaluation of Indium–111– and Yttrium–90–Labeled Linker–Immunoconjugates in Nude Mice and Dogs," *J. Nucl. Med. 34*:938–945 (Jun. 1993).

Ristamäki, R., et al., "Serum CD44 in Malignant Lymphoma: An Association With Treatment Response," *Blood 84*:238–243 (Jul. 1994).

Ristamäki, R., et al., "CD44v6 Expression in Non–Hodgkin's Lymphoma: an Association with Low Histological Grade and Poor Prognosis," *J. Pathol. 176*:259–267 (Jul. 1995).

Salles, G., et al., "Alternatively Spliced CD44 Transcripts in Diffuse Large–Cell Lymphomas: Characterization and Comparison With Normal Activated B Cells and Epithelial Malignancies," *Blood 82*:3539–3547 (Dec. 1993).

Screaton, G.R., et al., "Genomic structure of DNA encoding the lymphocyte homing receptor CD44 reveals at least 12 alternatively spliced exons," *Proc. Natl. Acad. Sci. USA 89*:12160–12164 (Dec. 1992).

Screaton, G.R., et al., "The Identification of a New Alternative Exon with Highly Restricted Tissue Expression in Transcripts Encoding the Mouse Pgp–1 (CD44) Homing Receptor," *J. Biol. Chem. 268*:12235–12238 (Jun. 1993).

Seiter, S., et al., "Prevention of Tumor Metastasis Formation by Anti–Variant CD44," *J. Exp. Med. 177*:443–455 (Feb. 1993).

Stamenkovic, I., et al., "A Lymphocyte Molecule Implicated in Lymph Node Homing Is a Member of the Cartilage Link Protein Family," *Cell 56*:1057–1062 (Mar. 1989).

Stauder, R., et al., "CD44 Variant Isoforms in Non–Hodgkin's Lymphoma: A New Independent Prognostic Factor," *Blood 85*:2885–2899 (May 1995).

Tanabe, K.K., et al., "Expression of CD44R1 adhesion molecule in colon carcinomas and metastasis," *Lancet 341*:725–726 (Mar. 1993).

Terpe, H.–J., et al., "CD44 variant inoforms are preferentially expressed in basal epithelial of non–malignant human fetal and adult tissues," *Histochemistry 101*:79–89 (Jan. 1994).

Thomas, G.D., et al., "Antibodies for tumour immunodetecting and methods for antibody radiolabelling," in *Antibodies. vol. II. A Practical Approach,* vol. II, Catty, D., ed., IRL Press, Oxford, UK, pp. 223–244 (1989).

Tölg, C., et al., "Splicing choice from ten variant exons establishes CD44 variability," *Nucl. Acids Res. 21*:1225–1229 (Mar. 1993).

Vriesendorp, H.M. et al., "Review of Five Consecutive Studies of Radiolabeled Immunoglobulin Therapy in Hodgkin's Disease," *Cancer Res. (Supp.) 55*:5888s–5892s (Dec. 1995).

Dialog File 351, Accession No. 95–052230/199507, Derwent WPI English language abstract for WO 95/00851 (Document AO1).

Dialog File 351, Accession No. 91–340908/199147, Derwent WPI English language abstract for EP 0 531 300 B1 (Document AP1).

Dialog File 351, Accession No. 93–136002/199317, Derwent WPI English lauguage abstract for EP 0 538 754 A2 (Document AL2).

* cited by examiner

SEQUENCE LISTING

<160> NUMBER OF SEQ ID NOS: 4

<210> SEQ ID NO 1
<211> LENGTH: 204
<212> TYPE: DNA
<213> ORGANISM: Homo sapiens
<220> FEATURE:
<221> NAME/KEY: CDS
<222> LOCATION: (3)..(203)

<400> SEQUENCE: 1

```
at agg aat gat gtc aca ggt gga aga aga gac cca aat cat tct gaa         47
   Arg Asn Asp Val Thr Gly Gly Arg Arg Asp Pro Asn His Ser Glu
    1               5                  10                  15 ggc tca act act tta ctg gaa ggt tat acc tct cat tac cca cac acg        95
Gly Ser Thr Thr Leu Leu Glu Gly Tyr Thr Ser His Tyr Pro His Thr
                20                  25                  30 aag gaa agc agg acc ttc atc cca gtg acc tca gct aag act ggg tcc       143
Lys Glu Ser Arg Thr Phe Ile Pro Val Thr Ser Ala Lys Thr Gly Ser
            35                  40                  45 ttt gga gtt act gca gtt act gtt gga gat tcc aac tct aat gtc aat       191
Phe Gly Val Thr Ala Val Thr Val Gly Asp Ser Asn Ser Asn Val Asn
        50                  55                  60 cgt tcc tta tca g                                                     204
Arg Ser Leu Ser
    65
```

<210> SEQ ID NO 2
<211> LENGTH: 67
<212> TYPE: PRT
<213> ORGANISM: Homo sapiens

<400> SEQUENCE: 2

```
Arg Asn Asp Val Thr Gly Gly Arg Arg Asp Pro Asn His Ser Glu Gly
  1               5                  10                  15

Ser Thr Thr Leu Leu Glu Gly Tyr Thr Ser His Tyr Pro His Thr Lys
             20                  25                  30

Glu Ser Arg Thr Phe Ile Pro Val Thr Ser Ala Lys Thr Gly Ser Phe
         35                  40                  45

Gly Val Thr Ala Val Thr Val Gly Asp Ser Asn Ser Asn Val Asn Arg
     50                  55                  60

Ser Leu Ser
 65
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 3
caggctggga gccaaatgaa gaaaatg                                          27

<210> SEQ ID NO 4
<211> LENGTH: 30
<212> TYPE: DNA
<213> ORGANISM: Artificial Sequence

```
<220> FEATURE:
<223> OTHER INFORMATION: Description of Artificial Sequence:  PCR Primer

<400> SEQUENCE: 4
tgataaggaa cgattgacat tagagttgga                                              30
```

METHOD FOR DIAGNOSIS AND THERAPY OF HODGKIN'S LYMPHOMAS

This application is the United States national application, filed under 35 U.S.C. §371, of PCT/EP97/07081 filed Dec. 17, 1997.

The present invention relates to processes for diagnosing and treating Hodgkin's lymphomas (lymphogranulomatosis) based on the expression of the variant exon v10 of the gene CD44 as the molecular target, agents for these processes and the use of these agents.

The highly glycosylated cell surface protein CD44 is involved in the interaction between cells and the extracellular matrix such as migration and activation of leukocytes in inflammation and immune monitoring, precursor formation of leukocytic and myeloid cells in bone marrow and also in the development of lymphoid organs and the interaction of cells with the extracellular matrix (Lesley et al., 1993, Günthert 1993, Pals et al., 1993, Mackay et al., 1994). The human CD44 gene is made up of at least 19 exons, of which at least 12 which code for the extracellular region are alternatively spliced (Screaton et al., 1992). The CD44 gene is transcribed in a number of normal tissues and carcinomas (Fox et al., 1994). Whereas the standard CD44 molecule (CD44s) is ubiquitously found expressed in epithelial and mesenchymal tissues, the various isoforms produced by alternative RNA splicing are found in very limited distribution (Heider et al., 1993). Some of the variant isoforms are involved in the activation of lymphocytes and occur in conjunction with metastasisation (Mackay et al., 1994, Günthert et al., 1991, Rudy et al., 1993, Koopman et al., 1993). Although the expression of variant CD44 has been shown to have a direct biological role in metastasis formation in carcinoma of the pancreas in rats (Günthert et al., 1991, Seiter et al., 1993), its role in human tumours is as yet unknown.

Various reports have been published showing that certain alternatively spliced forms of CD44 were expressed in human metastatic tumours (Heider et al., 1993 and 1996, Fox et al., 1994, Friedrichs et al., 1995, Kaufmann et al., 1995, Salles et al., 1993, Stauder et al., 1995, Koopman et al., 1993, Tanabe et al., 1993) Studies of the expression of CD44 in non-Hodgkin's lymphomas (NHL) concentrated on analysing the so-called lymphocyte homing receptor CD44H or CD44s (Horst et al., 1990a, Horst et al., 1990b, Jalkanen et al., 1991, Möller et al., 1992). Whereas some authors (Horst et al., 1990a, Jalkanen et al., 1991, Picker et al., 1988, Pals et al., 1989, Fujiwara et al., 1993) found a correlation between increased CD44s expression and unfavourable prognosis, other authors (Terpe et al., 1994) could not confirm these findings. Recently, upregulation of CD44v3 and CD44v6 isoforms was found in NHL with unfavourable pathological status (Koopman et al., 1993, Terpe et al , 1994, Salles et al., 1993, Stauder et al., 1995), whilst variant specific CD44-mAbs were used (Mackay et al., 1994, Koopman et al., 1993, Fox et al., 1993).

Various approaches have been developed for making use of the differential expression of variant exons of the CD44 gene in tumours and normal tissues f or diagnostic and therapeutic purposes (WO 94/02633, WO 94/12631, WO 95/00658, WO 95/00851, EP 0531300).

The aim of the present invention was to develop new methods of diagnosing and treating Hodgkin's lymphomas (lymphogranulomatosis) and preparing agents for such processes.

This aim is achieved by means of the present invention. It relates to processes for diagnosing and treating Hodgkin's lymphomas (lymphogranulomatosis) which are based on the expression of the variant exon v10 of the CD44 gene as a molecular marker or target. Antibody molecules of corresponding specificity are particularly suitable as vehicles for selectively reaching Hodgkin's lymphomas in vivo.

Preferred processes are characterised in that an antibody molecule is used which binds specifically to the amino acid sequence SEQ ID NO. 2 (see Sequence Listing).

Other aspects of the present invention are the use of antibody molecules of this kind in the processes according to the invention and agents for performing these processes.

The invention further relates to the use of an antibody molecule which is specific to an epitope within the amino acid sequence which is coded by the variable exon v10 of the CD44 gene, for preparing a pharmaceutical composition for the diagnosis and/or treatment of tumoral diseases. The tumoral disease in question is preferably Hodgkin's lymphoma (lymphogranulomatosis).

The invention further relates to an antibody molecule which is specific to an epitope within the amino acid sequence which is coded by the variable exon v10 of the CD44 gene for pharmaceutical use. Preferably, an antibody molecule of this kind is characterised in that it binds to SEQ ID NO. 2. It may be, in particular, a monoclonal antibody, an Fab- or F(ab')$_2$-fragment of an immunoglobulin, a recombinantly produced antibody, a recombinantly produced chimeric or humanised antibody or single chain antibody (scFv). Preferably, an antibody molecule of this kind is linked to a radioactive isotope, a radioactive compound, an enzyme, a toxin, a cytostatic, a prodrug, a cytokine or some other immunomodulatory polypeptide.

The nucleic and amino acid sequence of the variant exon v10 of the CD44 gene is known (Screaton et al., 1992, Tölg et al., 1993). These sequences are shown in the Sequence Listing (SEQ ID NO. 1 and 2). The existence of degenerate or allelic variants is unimportant to the performance of the invention; such variants are therefore expressly included.

The invention may be carried out with polyclonal or monoclonal antibodies specific to an epitope which is coded by the exon v10. The preparation of antibodies to known amino acid sequences can be carried out using methods known per se (Catty, 1989). For example, a peptide of this sequence may be prepared synthetically and used as an antigen in-an immunisation procedure. Another method is to prepare a fusion protein which contains the desired amino acid sequence, by integrating a nucleic acid (which may be prepared synthetically or, for example, by polymerase chain reaction (PCR) from a suitable probe) which codes for this sequence, into an expression vector and expressing the fusion protein in a host organism. The fusion protein, optionally purified, can then be used as an antigen in an immunisation procedure and insert-specific antibodies or, in the case of monoclonal antibodies, hybridomas which express insert-specific antibodies, are selected by suitable methods. Such methods are known in the art. Heider et al. (1993, 1996) and Koopman et al. (1993) describe the preparation of antibodies against variant epitopes of CD44.

However, for the process according to the invention, it is also possible to use antibody molecules derived from poly- or monoclonal antibodies, e.g. Fab- or F(ab')$_2$-fragments of immunoglobulins, recombinantly produced single chain antibodies (scFv), chimeric or humanised antibodies and other molecules which bind specifically to epitopes coded by exon v10. From a complete immunoglobulin it is possible for example to produce Fab-or F(ab')$_2$-fragments or other fragments (Kreitman et al., 1993). The skilled person is also capable of producing recombinant v10-specific antibody molecules. Corresponding methods are known in the art. Recombinant antibody molecules of this kind may, for example, be humanised antibodies (Shin et al., 1989; Gussow and Seemann, 1991), bispecific antibodies (Weiner et al., 1993; Goodwin, 1989), single chain antibodies (scFv, Johnson and Bird, 1991), complete or fragmentary immunoglobulins (Coloma et al., 1992; Nesbit et al., 1992; Barbas et al., 1992), or antibodies produced by chain shuffling (Winter et al., 1994). Humanised antibodies may be produced for example by CDR grafting (EP 0239400). Framework regions may also be modified (EP 0519596). In order to humanise antibodies, nowadays it is possible to use methods such as PCR (cf. for example EP 0368684; EP 0438310; WO 9207075) or computer modelling (cf. for example WO 9222653). It is also possible to prepare and use fusion proteins such as single chain antibody/toxin fusion proteins (Chaudhary et al., 1990; Friedman et al., 1993). The headings "antibody" and "antibody molecules" should include, in addition to polyclonal and monoclonal antibodies, all the compounds discussed in this section as well as other compounds which are structurally derived from immunoglobulins and can be prepared by methods known per se.

For diagnostic purposes, antibody molecules may be linked, for example, to radioactive isotopes such as $^{131}$I, $^{111}$In, $^{99m}$Tc or radioactive compounds (Larson et al., 1991; Thomas et al., 1989; Srivastava, 1988), enzymes such as peroxidase or alkaline phosphatase (Catty and Raykundalia, 1989), with fluorescent dyes (Johnson, 1989) or biotin molecules (Guesdon et al., 1979). For therapeutic applications, v10-specific antibody molecules may be linked to radioisotopes such as $^{90}$Y, $^{111}$In, $^{131}$I or $^{168}$Re (Quadri et al., 1993; Lenhard et al., 1985, Vriesendorp et al., 1991; Wilbur et al., 1989), toxins (Vitetta et al., 1991; Vitetta and Thorpe, 1991; Kreitman et al., 1993; Theuer et al., 1993), cytostatics (Schrappe et al., 1992), prodrugs (Wang et al., 1992; Senter et al., 1989) or radioactive compounds. The antibody may also be linked to a cytokine or another immunomodulatory polypeptide, e.g. tumour necrosis factor or interleukin-2.

Advantageously, the diagnostic process according to the invention can be used to examine samples from patients, e.g. from biopsies, where there is a suspicion of Hodgkin's lymphoma (lymphogranulomatosis) or where this has already been diagnosed but the tumour requires more accurate characterisation. Variant CD44 molecules which contain an amino acid sequence coded by the variable exon v10 can be detected at the protein level by means of antibodies or at the nucleic acid level by means of specific nucleic acid probes or primers for polymerase chain reaction (PCR). The invention consequently also relates to antibody molecules and nucleic acids which are suitable as probes or primers for such processes, and the use of these antibodies and nucleic acids for the diagnosis and analysis of Hodgkin's lymphomas. For example, tissue sections can be investigated immunohistochemically with antibodies using methods known per se. Extracts or body fluids obtained from tissue samples can also be investigated by other immunological methods using antibodies, e.g. by Western blots, enzyme-linked immunosorbant assays (ELISA, Catty and Raykundalia, 1989), radioimmunoassays (RIA, Catty and Murphy, 1989) or related immunoassays. The samples may be investigated qualitatively, semiquantitatively or quantitatively. The expression of the CD44-splice variant v10 in Hodgkin's disease is associated with aggressive behaviour of the tumour and a high risk of recurrence. This correlates with an advanced stage and poor prognosis of NSHD (nodular sclerosis Hodgkin's disease).

As well as in vitro diagnosis, antibody molecules with specificity according to the invention are also suitable for in vivo diagnosis of Hodgkin's lymphomas. If the antibody molecule carries a detectable label, the label can be detected for diagnostic purposes, e.g. imaging the tumour in vivo or for radioguided surgery, for example. For using antibodies conjugated with radioactive isotopes for immunoscintigraphy (imaging), for example, there are a number of procedures on the basis of which the skilled person can perform the invention (Siccardi et al., 1989; Keenan et al., 1987; Perkins and Pimm, 1992; Colcher et al., 1987; Thompson et al., 1984).

Data obtained by detecting and/or quantifying the expression of the variant CD44 epitope v10 can thus be used for diagnosis and prognosis. It may be advantageous to combine such data with other prognostic parameters, e.g. with the grade of tumour.

Antibody molecules with the specificity according to the invention and optionally linked with a cytotoxic agent may advantageously be used to treat Hodgkin's lymphomas (lymphogranulomatosis). They may be administered systemically or topically, e.g. by intravenous route (as a bolus or continuous infusion), or by intraperitoneal, intramuscular or subcutaneous injection/infusion. Methods of administering conjugated or non-conjugated antibodies, e.g. complete immunoglobulins, fragments, recombinant humanised molecules etc., are known in the art (Mulshine et al., 1991; Larson et al., 1991; Vitetta and Thorpe, 1991; Vitetta et al., 1991; Breitz et al., 1992, 1995; Press et al., 1989; Weiner et al., 1989; Chatal et al., 1989; Sears et al., 1982).

The antibody molecules may be formulated in a manner known per se. For example, they may be present in aqueous solution, optionally buffered with a physiologically acceptable buffer. A solution of this kind may be characterised by the addition of suitable stabilisers and adjuvants. However, the antibody molecules may also be present in the form of a freeze-dried preparation (lyophilisate) which is reconstituted with a suitable solvent, e.g. water, before use.

In a preferred embodiment of therapeutic application, a humanised v10-specific immunoglobulin or an F(ab')$_2$-fragment thereof is linked with $^{90}$Y (Quadri et al., 1993; Vriesendorp et al., 1995), $^{131}$I (Juweid et al., 1995; Press et al., 1995; Thomas et al., in: Catty 1985, p. 230–239), $^{186}$Re (Breitz et al., 1992, 1995) or another suitable radioisotope and used for radioimmunotherapy of Hodgkin's lymphomas. For example, an antibody molecule of this kind may be linked with $^{90}$Y using a chelating linker such as ITCB-DTPA (isothiocyanatobenzyl-diethylenetriamine pentacetate), whilst a specific activity of 5–20 mCi/mg, preferably 10 mCi/mg should be achieved. This agent can then be administered to a patient with an antigen-positive tumour in a dosage of 0.1 to 1 mCi/kg of body weight, preferably 0.3 to 0.5 mCi/kg of body weight, most preferably 0.4 mCi/kg. When the total quantity of protein to be administered is from 2 to 5 mg this may be given in the form of a rapid intravenous bolus injection. In the case of monoclonal antibodies it may be necessary to mix the agent with an excess (e.g. a ten-fold molar excess) of the non-radioactive antibody before administering it; in this case, the preparation is better administered in the form of an intravenous infusion over a period of 15 minutes, for example. The application can be repeated. The treatment can be backed up by bone marrow transplantation.

FIGURES

FIG. 1: A. Individual HRS (Hodgkin and Reed-Sternberg) cells of a patient with no recurrence, reacting with mAb VFF16 (CD44v10). The arrow tips point to non-reactive HRS cells. B. >50% of the HRS cells of patients with a recurrence show reactivity (ABC,×400).

Figure 2:
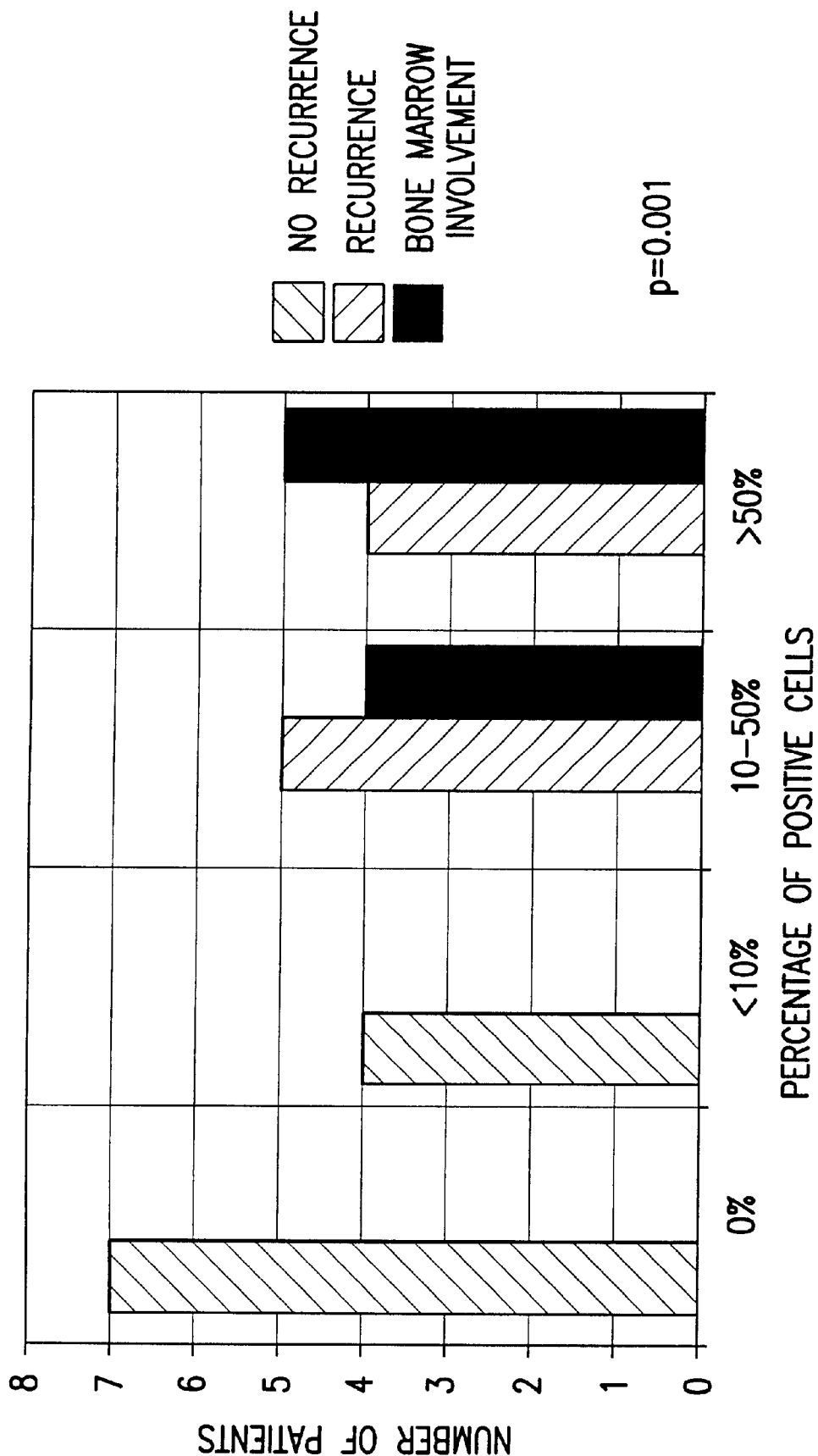

FIG. 2: CD44v10 expression in HRS cells in various patient groups. It should be noted that patients with a poor clinical progress, i.e. recurrence or bone marrow involvement, exclusively show more than 10% positive HRS cells, whereas patients with no recurrence have less than 10% positive HRS cells. The difference between these two groups is statistically highly significant.

Figure 3:
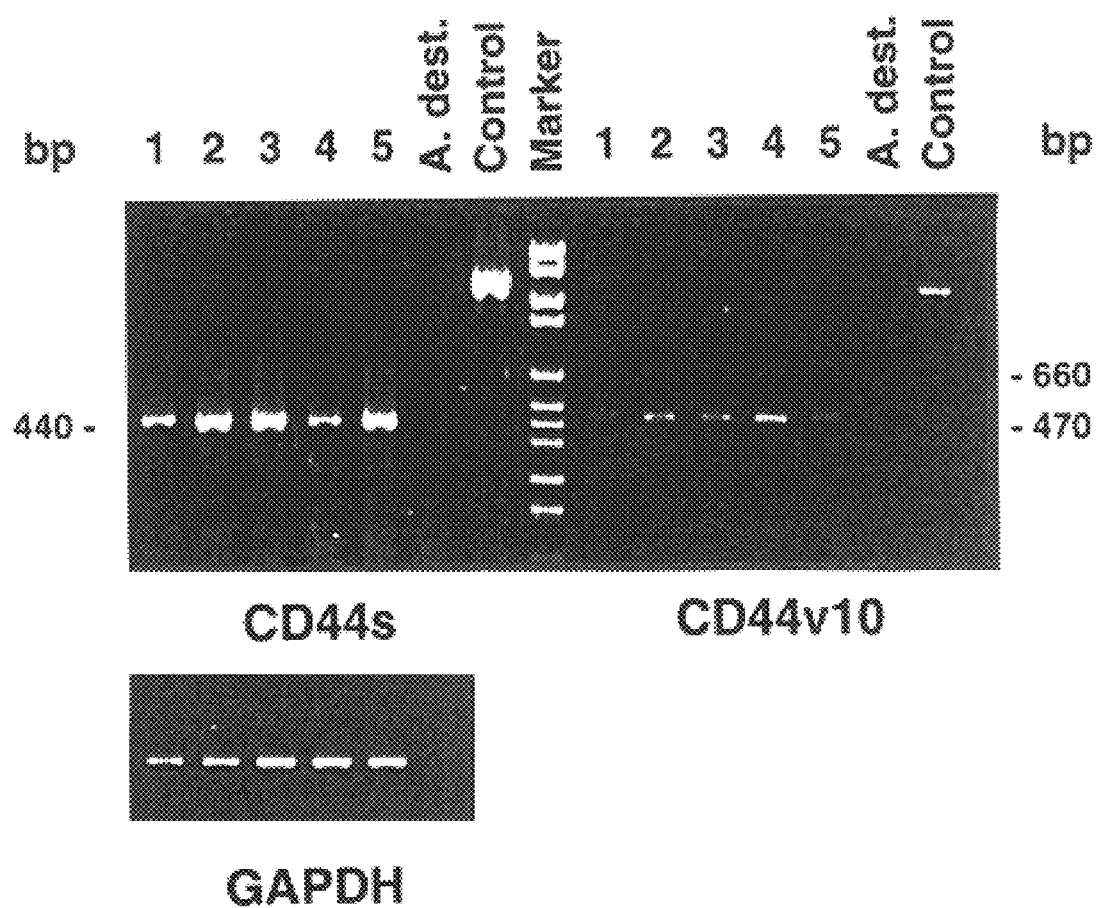

FIG. 3: RT-PCR analysis using CD44v10-specific primers (right half): the main transcript of about 470 bp in all the probes and a weaker transcript of 660 bp in probes 2, 3 and 4 indicate CD44v10-containing isoforms in all 5 cases. A dominant band of 440 bp when using primers which are specific to the 5'- and 3'-constant region indicates the standard form of CD44 (left half).

EXAMPLES

Example 1

Preparation of v10-specific Antibodies

The entire variant region of the HPKII type of CD44v (Hofmann et al., 1991) was amplified from human keratinocyte cDNA by polymerase chain reaction (PCR). The two PCR primers 5'-CAGGCTGGGAGCCAAATGAAGAAAATG-3', (SEQ ID NO:3), positions 25–52, and 5'-TGATAAGGAACGATTGACATTAGAGTTGGA-3', (SEQ ID NO:4), positions 1013–984 of the LCLC97-variant region as described by Hofmann et al. contained an EcoRI recognition site which was used to clone the PCR product directly into the vector pGEX-2T (Smith et al., 1988). The resulting construct (pGEX CD44v HPKII, v3–v10) codes for a fusion protein of ~70 kD, consisting of glutathione-S-transferase from *Schistosoma japonicum* and the exons v3–v10 from human CD44 (Heider et al., 1993). The fusion protein was expressed in *E. coli* and then affinity-purified over glutathione-agarose (Smith et al., 1988).

Female Balb/c mice were immunised by intraperitoneal route with the affinity-purified fusion protein according to the following plan:

$1^{st}$ immunisation: 90 μg of fusion protein in complete Freund's adjuvant $2^{nd}$ and $3^{rd}$ immunisations: 50 μg of fusion protein in incomplete Freund's adjuvant.

The immunisations were carried out at intervals of 4 weeks. 14 days after the last immunisation, the animals were immunised on three successive days with 10 μg of fusion protein in PBS. The next day, spleen cells from an animal with a high antibody titre were fused with P3.X63-Ag8.653 murine myeloma cells using polyethyleneglycol 4000. The hybridoma cells were then selected in microtitre plates in HAT medium (Köhler and Milstein, 1975; Kearney et al., 1979).

The antibody titre in the serum and the screening of the hybridoma supernatants were carried out using an ELISA. In this test, first of all, microtitre plates were coated with fusion protein (GST-CD44v3-10) or with glutathione-S-transferase on its own. Then they were incubated with serial dilutions of serum samples or hybridoma supernatants and the specific antibodies were detected with peroxidase-conjugated antibodies against murine immunoglobulin. Hybridomas which reacted only with glutathione-S-transferase were discarded. The remaining antibodies were characterised first in an ELISA with domain-specific fusion proteins (exon v3, exon v5+v6, exon v6+v7, exon v8–v10, exon v10) (Koopman et al., 1993). Their immunohistochemical reactivity was tested on sections of human skin.

Antibodies from the supernatants of the hybridoma clones VFF-14 and VFF-16 bind only to fusion proteins containing a domain which is coded by the exon v10.

Example 2

Immunohistochemical Examination of Tissue Samples

Tissue and patients

37 Paraffin-embedded lymph node samples from 29 patients with NSHD (nodular sclerosis Hodgkin's disease; according to Rye classification) were obtained from the collection of the Pathology Department, University Medical School, Graz, Austria, and divided into three groups; group 1: 11 patients with pretreated NSHD before treatment (5 patients at stage I, 6 at stage II), who had been free from recurrence for more than 6 years; group 2: 9 patients with pretreated NSHD before treatment (4 at stage I, 5 at stage II) suffered a recurrence of the disease in one to three years. Two to three follow-up lymph node sections of NSHD recurrences from 7 of these 9 patients were also included in this study; group 3: 9 patients with bone marrow involvement at the time of the original diagnosis (stage IV).

Immunohistochemistry

The lymph node samples were stained with the following mabs: CD44 standard (s) recognised by the mAb SFF2; CD44v5 detected by the mAb VFF8; CD44v6 detected by the mabs VFF7 and VFF18; CD44v10 detected by the mAbs VFF14 and VFF16. Mab SFF2 recognises an epitope common to all CD44-isoforms. Mabs VFF7 and VFF18 recognise different but overlapping epitopes which are coded by the exon v6. Mab VFF8 is specific to exon v5. Mabs VFF14 and VFF16 react with an epitope which is coded by exon v10.

The immunohistochemistry was carried out on sections treated with microwaves (Gerdes et al., 1992), using the avidin-biotin complex (ABC) peroxidase method (Guesdon et al., 1979). Paraffin sections were dewaxed in xylene, rehydrated and the endogenous peroxidase was blocked with $H_2O_2$ in methanol. The slides were placed in a glass stand and wetted in 500 ml of 0.01 M citrate buffer (2.1 g of citric acid in 1 litre of deionised water, pH adjusted to 6.0 using 2 N NaOH). The microwave treatment was carried out for 35 hours at maximum power (600 W) in a microwave oven (BioRad). After 9 minutes' microwave treatment the evaporated buffer was topped up with deionised water. After the microwave irradiation the solution was cooled for 20 minutes. Then the slides were rinsed in phosphate-buffered saline (PBS) and immunostained by diaminobenzidine (DAB) development.

For comparison, 10 frozen lymph node samples (3 from patients of group 1, 2 from group 2 and 5 recently collected cases) were also incubated with the mabs VFF14 (v10) and VFF16 (v10), using the alkaline phosphatase-anti-alkaline phosphatase (APAAP) method (Cordell et al., 1984).

For control purposes, sections of normal human epidermis which is known to contain the antigens in question were tested (positive controls). Replacement of the primary antibody by normal serum always produced negative results (negative controls).

As an additional control, immunohistochemical staining for CD44v10 and CD44v6 expression was repeated twice in each case. To confirm the findings, the cases were additionally incubated in a different laboratory using the APAAP method (Cordell et al., 1984).

The percentage of HRS (Hodgkin and Reed-Sternberg) cells stained with the antibodies was graded as ok, less than 10%, 10–50% and over 50%. Care was taken to ensure that the immunoreactive HRS cells were clearly tumour cells (e.g. by looking for the presence of characteristic nuclear details), particularly in those cases where less than 10% of the HRS cells expressed the antigens in question. All the cases were assessed separately by two of the inventors. The spread of the staining, e.g. on the membrane, in the cytoplasm or both, was recorded, as well as the immunoreactivity in cells which were not HRS cells.

Statistical analysis

CD44 expression patterns were analysed using the Pearson-chi-square calculation and the Mantel-Haenszel test for linear association, by means of the program SPSS for Windows. P-values less than or equal to 0.05 were regarded as significant.

Results of the immunohistochemical staining

Table 1 shows a summary of the results obtained with antibodies directed against CD44s, CD44v5, v6 and v10 in HRS cells. The majority of the antigenic reactivity of the HRS cells was on the cell surface in every case. A variable number of HRS cells yielded cytoplasmic and/or dot-like perinuclear reactivity with or without surface staining, which probably reflected the reactivity of CD44 molecules in the Golgi apparatus or in the endoplasmic reticulum.

Figure 1B:
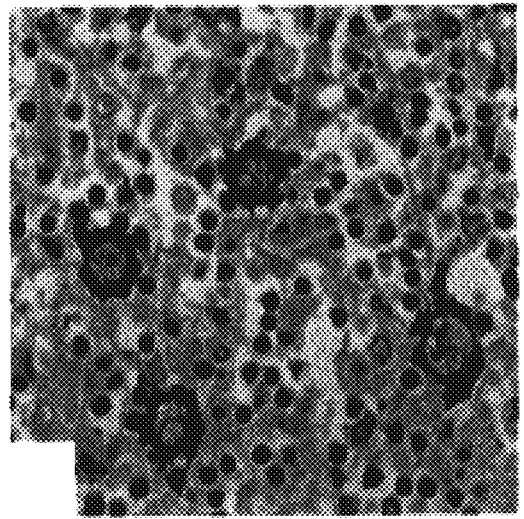

CD44v10 expression correlates with an advanced stage and poor prognosis of NSHD. CD44s-, CD44v5-(detected by mAb VFF8) and CD44v6-expression (detected by mAb VFF18) in HRS cells was found in the majority of cases, although there was great variation in the number of stained cells (Table 1). CD44v6 expression (detected by mAb VFF7) was found in only a few cases and, when present, was restricted to a minority of HRS cells (Table 1). In patients with no recurrence, CD44v10 expression (detected by the mAbs VFF14 and VFF16) was found in only a very few cases, and the proportion of reactive HRS cells was <10% (FIGS. 1A and 2). By contrast, in every case of a patient with a recurrence or initial involvement of the bone marrow, CD44v10 expression was found. In the majority of these cases, there was a clear overexpression of CD44v10 with >50% reactive HRS cells (FIGS. 1B and 2). This overexpression of CD44v10 was also found in the lymph node sections of recurrences studied (Table 2).

Frozen lymph node sections from 3 patients with no recurrence and from 2 patients with a recurrence yielded exactly the same results as paraffin sections. The two antibodies specific to exon v10 (VFF14 and VFF16) showed identical results in the reaction either on the surface and/or in the cytoplasm of the HRS cells.

Using Fisher's exact test, the differences in the CD44 isoform expression between groups of patients with non-aggressive and aggressive NSHD yielded the following p-values: CD44s (p=0.3625), CD44v5 (p=0.2415), CD44v6 (detected with mAb VFF7) (p=0.2903), CD44v6 (detected by mAb VFF18) (p=0.1836), CD44v10 (detected by mAbs VFF14 and VFF16) (p=0.001). This shows that the different expression patterns of CD44v10 (detected by mAbs VFF14 and VFF16) within these NSHD groups were statistically highly significant. The expression of the CD44 splice variant v10 in Hodgkin's disease is associated with aggressive behaviour of the tumour and a high risk of recurrence. It correlates with an advanced stage and-poor prognosis of NSHD.

By contrast with earlier immunohistochemical studies of CD44 expression in conjunction with prognostic relevance in neoplasia of different histogenetic origin, which were carried out exclusively on frozen sections (Koopman et al., 1993, Terpe et al., 1994; Ristamaki et al., 1994, 1995, Stauder et al., 1994, Heider et al., 1993, Horst et al., 1990a,b, Heider et al., 1996, Kaufmann et al., 1995, Mulder et al. 1994), the present invention was able to demonstrate that CD44-mAbs can also be used on paraffin-embedded material if microwave treatment is used. This process requires constant fixing and microwave treatment in order to give reproducible results. In order to validate the immunoreactivity obtained with paraffin-embedded material, the immunohistochemical analysis was carried out in parallel on frozen samples and identical results were obtained. In addition, the results of the CD44v10 expression were confirmed by RT-PCR. For the CD44v6 expression, a correlation could be demonstrated with poor prognosis in NHL (Koopman et al., 1993, Salles et al., 1993, Terpe et al., 1994, Ristamaki et al., 1994, Stauder et al., 1994), breast cancer (Kaufmann et al., 1995) and colon carcinomas (Heider et al., 1993). In the cases of NSHD which we investigated, however, only a few cases were CD44v6-positive and we could not detect any correlation with the prognosis, using two different antibodies against CD44v6. Because these two mabs used against v6 recognise different epitopes of the exon v6-coded amino acid sequence, this absence of detectable CD44v6 in the majority of cases (see Table 1) cannot be explained by modification or masking of epitopes. By contrast with the frequent expression of CD44v5 in gastric adenocarcinomas (Heider et al., 1993) the data relating to CD44v5 expression within the three groups of NSHD were not statistically significant.

Exon v10, in addition to exons v3 and v6, is a variant exon which is constitutively expressed in lymphocytes (Stauder et al., 1994). Up till now, CD44v10 expression in NHLs has not been systematically analysed and this exon has only rarely been detected in carcinomas (Heider et al., 1996). The present invention demonstrates, by the example of two different antibodies against CD44v10 (VFF14 and VFF16), a statistically significant high regulation of CD44v10 expression in HRS cells of NSHD with a poor prognosis (groups 2 and 3). Both exon v10-specific antibodies showed identical results, both on the surface and also (and/or) in the cytoplasm of the HRS cells. The detection of CD44v10 expression with two different mabs is important because, for example, in breast cancer different data were obtained by different authors using different mkbs of the same exon specificity (Friedrichs et al., 1995, Kaufmann et al., 1995). To confirm our surprising results still further, all the cases were independently immunostained in a different laboratory (using a different staining method), with identical results.

The results for the CD44v10 expression in HRS cells of NSHD are the first data which show a correlation between CD44v10 expression and the stage and prognosis of the disease. The methods according to the invention thus provide the doctor with valuable diagnostic and prognostic information on Hodgkin's lymphoma. Moreover, CD44v10 is a suitable molecular target for therapeutic interventions in this disease.

TABLE 1

Reactivity of HRS cells

| Patients | CD44s SFF2 | | v5 VFF8 | | v6 VFF7 | | v6 VFF18 | | v10 VFF14 | | v10 VFF16 | |
|---|---|---|---|---|---|---|---|---|---|---|---|---|
| | n | % | n | % | n | % | n | % | n | % | n | % |
| Group 1 n = 11 | | | | | | | | | | | | |
| >50 | 3 | 27.3 | 0 | 0 | 0 | 0 | 1 | 9.1 | 0 | 0 | 0 | 0 |
| 10–50 | 3 | 27.3 | 1 | 9.0 | 0 | 0 | 0 | 0 | 0 | 0 | 0 | 0 |
| <10 | 3 | 27.3 | 6 | 54.5 | 2 | 18.2 | 8 | 72.7 | 4 | 36.4 | 4 | 36.4 |
| 0 | 2 | 18.1 | 4 | 36.5 | 9 | 81.8 | 2 | 18.2 | 7 | 63.6 | 7 | 63.6 |
| Group 2 n = 9 | | | | | | | | | | | | |
| >50 | 2 | 22.2 | 1 | 11.1 | 0 | 0 | 1 | 11.0 | 4 | 44.4 | 4 | 44.4 |
| 10–50 | 5 | 55.6 | 1 | 11.1 | 1 | 11.1 | 4 | 44.5 | 5 | 55.6 | 5 | 55.6 |
| <10 | 2 | 22.2 | 7 | 77.8 | 3 | 33.3 | 4 | 44.5 | 0 | 0 | 0 | 0 |
| 0 | 0 | 0 | 0 | 0 | 5 | 55.6 | 0 | 0 | 0 | 0 | 0 | 0 |
| Group 3 n = 9 | | | | | | | | | | | | |
| >50 | 0 | 0 | 0 | 0 | 0 | 0 | 0 | 0 | 5 | 55.6 | 5 | 55.6 |
| 10–50 | 6 | 66.7 | 1 | 11.1 | 1 | 11.1 | 2 | 22.2 | 4 | 44.4 | 4 | 44.4 |
| <10 | 3 | 33.3 | 8 | 88.9 | 0 | 0 | 7 | 77.8 | 0 | 0 | 0 | 0 |
| 0 | 0 | 0 | 0 | 0 | 8 | 88.9 | 0 | 0 | 0 | 0 | 0 | 0 |

TABLE 2

Reactivity (%) of CD44v10 (VFF14 and VFF16) and CD44v6 (VFF18) in HRS cells of patients of group 2 (recurrence)

| Patients | CD44v10 (VFF14) | CD44v10 (VFF16) | CD44v6 (VFF18) |
|---|---|---|---|
| 1 | >50 | >50 | 10–50 |
| 1 recurrence | 10–50 | 10–50 | 10–50 |
| 1 recurrence | 10–50 | 10–50 | 10–50 |
| 2 | >50 | >50 | 10–50 |
| 2 recurrence | 10–50 | 10–50 | 10–50 |
| 3 | 10–50 | 10–50 | <10 |
| 3 recurrence | 10–50 | 10–50 | <10 |
| 4 | 10–50 | 10–50 | <10 |
| 4 recurrence | 10–50 | 10–50 | >50 |
| 5 | 10–50 | 10–50 | 10–50 |
| 5 recurrence | 10–50 | 10–50 | 10–50 |
| 6 | >50 | >50 | <10 |
| 6 recurrence | >50 | >50 | 10–50 |
| 7 | >50 | >50 | <10 |
| 7 recurrence | 10–50 | 10–50 | <10 |
| 8 | 10–50 | 10–50 | 10–50 |
| 9 | 10–50 | 10–50 | >50 |

Example 3

Use of v10-specific RT-PCR for Diagnostic Purposes

Reverse transcription polymerase chain reaction (PCR)

Five cases enabled mRNA to be isolated and were additionally analysed by reverse transcriptase polymerase chain reaction (RT-PCR).

1 μg of total RNA was isolated and reverse transcribed as described in the literature (Gunthert et al., 1991). 5 μl of first strand cDNA were amplified with Taq polymerase (Promega, Madison, USA) in a volume of 50 μl, using the buffer conditions recommended by the manufacturer. The concentration of primer was 0.2 mM. In order to test the quality and frequency of cDNA synthesis, a GAPDH-PCR was carried out with oligonucleotides which were homologous to positions 8–29 and 362–339 of the published GAPDH-cDNA sequence (Allen et al., 1987). Pre-incubation for 5 minutes at 95° C. was followed by 25 amplification cycles (30 seconds at 95° C., 1.5 minutes at 62° C.) and an extension cycle of 7 minutes at 72° C. Then 10 μl of the reaction were analysed on a 2% agarose gel and the amplification product was inspected under UV light after the gel had been stained with ethidium bromide. In order to amplify cDNAs containing CD44v10, primers were used which were homologous with the 3'-end of exon v10 (positions 986–1013, Hofmann et al., 1991) and with the 5'-constant region of CD44 (positions 513–540, Stamenkovic et al., 1989). In order to amplify isoforms containing CD44 standard, a 3'-constant CD44 primer (positions 934–958, Stamenkovic et al., 1989) was used instead of the CD44v10-specific primer. After 40 amplification cycles (94° C. for 30 seconds, 62° C. for 1.5 minutes), 10 μl of the reaction mixture were analysed as above. For control purposes, instead of RNA, either distilled water was used (negative control) or a plasmid containing CD44v3-v10 was used (positive control, Heider et al., 1996).

In the 5 cases in which it was possible to isolate RNA, the RT-PCR analysis confirmed the expression of CD44v10 containing CD44-isoforms (as they were samples which had only recently been obtained, the further progress of the disease in these patients is not yet known). The amplified fragments correspond to CD44 transcripts which contain the constant-proportion of CD44 combined with the variant exon v10 (460 bp band) or variant exon v10 plus other variant exons (660 bp band) (FIG. 3, right half). For control purposes, parallel cDNAs were amplified with primers which were specific for the 5'- and 3'-constant region of CD44 (FIG. 3, left hand side), obtaining a prominent band of 440 bp which indicates the standard form of CD44. The molecular-genetic results correlated with the immunohistochemical findings, where in all 5 cases a high proportion of the HRS cells (which represented less than 10% of the total number of cells in a sample) expressed CD44v10 and the majority of the cells (HRS plus non-tumour cells) reacted with the anti-CD44s antibody.

LITERATURE

Allen R W, Trach K A, Hoch J A. Identification of the 37-kDa protein displaying a variable interaction with the erythroid cell membrane as glyceraldehyde-3-phosphate dehydrogenase. *J.Biol. Chem.* 262 (2): 649–653 (1987).

Barbas C F, Björling E, Chiodi F, Dunlop N, Cababa D, Jones T M, Zebedee S L, Persson M A A, Nara P L, Norrby E, Burton D R. Recombinant human Fab fragments neutralize human type 1 immunodeficiency virus in vitro. *Proc. Natl. Acad. Sci. USA*. 89: 9339–9343 (1992).

Breitz H B, Weiden P L, Vanderheyden J-L, Appelbaum J W, Bjorn M J, Fer M F, Wolf S B, Ratcliff B A, Seiler C A, Foisie D C, Fisher D R, Schroff R W, Fritzberg A R, Abrams P G. Clinical experience with rhenium-186-labeled monoclonal antibodies for radioimmunotherapy: results of phase I trials. *J. Nucl. Med* 33: 1099–1112 (1992).

Breitz H B, Durham J S, Fisher D R, Weiden P L, DeNardo G L, Goodgold H M, Nelp W B. Phrmacokinetics and normal organ dosimetry following intraperitoneal rhenium-186-labeled monoclonal antibody. *J. Nucl. Med* 36: 754 (1995).

Catty, D (Editor). *Antibodies Vols. I and II.* IRL Press Oxford (1989).

Catty, D., Raykundalia, C. ELISA and related immunoassays. In: Catty, D (Editor). *Antibodies Vol. II*. IRL Press Oxford (1989), 97–152, see pages 105–109.

Catty, D., Murphy, G. Immunoassays using radiolabels. In: Catty, D (Ed.). *Antibodies Vol. II*. IRL Press Oxford (1989), 77–96.

Chatal J-F, Saccavini J-C, Gestin J-F, Thédrez P, Curtet C, Kremer M, Guerreau D, Nolibe D, Fumoleau P, Guillard Y. Biodistribution of indium-111-labeled OC 125 monoclonal antibody intraperitoneally injected into patients operated on for ovarian carcinomas. *Cancer Res*. 49: 3087–3094 (1989).

Chaudhary V K, Batra J K, Galdo M G, Willingham M C, Fitzgerald D J, Pastan I. A rapid method of cloning functional variable-region antibody genes in Escherichia coli as single-chain immunotoxins. *Proc. Natl. Acad Sci. U.S.A*. 87: 1066 (1990).

Colcher D, Esteban J, Carrasquillo J A, Sugarbaker P, Reynolds J C, Bryant G, Larson S M, Schlom J. Complementation of intracavitary and intravenous administration of a monoclonal antibody (B72.3) in patients with carcinoma. *Cancer Res*. 47: 4218–4224 (1987).

Coloma M J, Hastings A, Wims L A, Morrison S L. Novel vectors for the expression of antibody molecules using variable regions generated by polymerase chain reaction. *J. Immunol. Methods* 152: 89–104 (1992).

Cordell J L, Falini B, Erber W N, Ghosh A K, Abdulaziz Z, MacDonald S, Pulford K A, Stein H, Mason D Y. Immunoenzymatic labeling of monoclonal antibodies using immune complexes of alkaline phosphatase and monoclonal anti-alkaline phosphatase (APAAP complexes). *J. Histochem. Cytochem*. 32 (2): 219–229 (1984).

Fox S B, Gatter K C, Jackson D G, Screaton G R, Bell M V, Bell J I, Harris A L, Simmons D, Fawcett J. CD44 and cancer screening. *Lancet* 342 (8870): 548–549 (1993).

Fox S B, Fawcett J, Jackson D G, Collins I, Gatter K G, Harris A L, Gearing A, Simmons D I. Normal human tissues, in addition to some tumors, express multiple different CD44 isoforms. *Cancer Res* 54: 4539–4546 (1994)

Friedmann P N, McAndrew S J, Gawlak S L, Chace D, Trail P A, Brown J P, Siegall C B. BR96 sFv-PE40, a potent single-chain immunotoxin that selectively kills carcinoma cells. *Cancer Res*. 53: 334–339 (1993).

Friedrichs K, Franke F, Lisboa B W, Kugler G, Gille I, Terpe H J, Holzel F, Maass H, Günthert U. CD44 isoforms correlate with cellular differentiation but not with prognosis in human breast cancer. *Cancer Res*. 55(22): 5424–5433 (1995).

Fujiwara K, Yoshino T, Miyake K, Ohara N, Akagi T. Expression of a lymphocyte adhesion molecule (CD44) in malignant lymphomas:relevance to primary site, histological subtype and clinical stage. *Acta Med. Okayama* 47 (3): 215–222 (1993).

Gerdes J, Becker M H, Key G, Cattoretti G. Immunohistological detection of tumour growth fraction (Ki-67 antigen) in formalin-fixed and routinely processed tissues. *J. Pathol*. 168 (1): 85–86 (1992).

Goodwin D A. A new appoach to the problem of targeting specific monoclonal antibodies to human tumors using anti-hapten chimeric antibodies. *J. Nucl. Med. Biol*. 16: 645 (1989).

Günthert, U., Hofmann, M., Rudy, W., Reber, S., Zöller, M., HauBmann, I., Matzku, S., Wenzel, A., Ponta, H., and Herrlich, P. A new variant of glycoprotein CD44 confers metastatic potential to rat carcinoma cells. *Cell* 65: 13–24 (1991).

Günthert U. CD44: a multitude of isoforms with diverse functions. *Curr. Top. Microbiol. Immunol* 184: 47–63 (1993).

Guesdon, J. I., Ternynck, T., Avrameas, S. *J. Histochem. Cytochem*. 27: 1131 (1979).

Güfssow D, Seemann G. Humanization of monoclonal antibodies. *Methods Enzymol*. 203: 99–121 (1991):

Heider, K.-H., Hofmann, M., Horst, E., van den Berg, F., Ponta, H., Herrlich, P., and Pals, S. T. A human homologue of the rat metastasis-associated variant of CD44 is expressed in colorectal carcinomas and adenomatous polyps. *J. Cell Biol*. 120: 227–233 (1993).

Heider, K.-H., Mulder, J.-W. R., Ostermann, E., Susani, S., Patzelt, E., Pals, S. T., Adolf, G. R. Splice variants of the cells surface glycoprotein CD44 associated with metastatic tumor cells are expressed in normal tissues of humans and cynomolgus monkeys. *Eur. J. Cancer* 31A: 2385–2391 (1995).

Heider K H, Ratschek M, Zatloukal K, Adolf G R. Expression of CD44 isoforms in human renal cell carcinomas. *Virchows Arch*. 428: 267–273 (1996).

Hofmann, M., Rudy, W., Zoller, M., Tolg, C., Ponta, H., Herrlich P., and Gunthert, U. CD44 splice variants confer metastatic behavior in rats: homologous sequences are expressed in human tumor cell lines. *Cancer Res*. 51: 5292–5297 (1991).

Horst E, Meijer C J, Radaszkiewicz T, Ossekoppele G J, Van Krieken J H, Pals S T. Adhesion molecules in the prognosis of diffuse large-cell lymphoma: expression of a lymophocyte homing receptor (CD44), LFA-1 (CD 11a/18), and ICAM-1 (CD54). *Leukemia* 4 (8): 595–599 (1990a).

Horst E, Meijer C J, Radaskiewicz T, van Dongen J J, Pieters R, Figdor C G, Hooftman A, Pals S T. Expression of a human homing receptor (CD44) in lymphoid malignancies and related stages of lymphoid development. *Leukemia* 4 (5): 383–389 (1990b).

Jalkanen S, Joensuu H, Soderstrom K O, Klemi P. Lymphocyte homing and clinical behavior of non-Hodgkin's lymphoma. *J. Clin. Invest*. 87 (5): 1835–1840 (1991).

Johnson, G D. Immunofluorescence. In: Catty, D (Ed.). *Antibodies Vol. II*. IRL Press Oxford (1989), 179–200, see pages 180–189.

Johnson S, Bird R E. Construction of single-chain derivatives of monoclonal antibodies and their production in *Escherichia coli. Methods Enzymol.* 203: 88–98 (1991).

Juweid M, Sharkey R M, Markowitz A, Behr T, Swayne L C, Dunn R. Hansen H J, Shevitz J, Leung S-O, Rubin A D, Herskovic T. Hanley D, Goldenberg D M. Treatment of Non-Hodgkins's lymphoma with radiolabeled murine, chimeric, or humanized LL2, an anti-CD22 monoclonal antibody. *Cancer Res.* (Suppl.) 55: 5899s–5907s (1995).

Kaufmann M, Heider K H, Sinn H P, von Minckwitz G, Ponta H, Herrlich P. CD44 variant exon epitopes in primary breast cancer and length of survival. *Lancet* 345 (8950): 615–619 (1995).

Kearney, J. F, Radbruch A., Liesegang B., Rajewski K. A new mouse myeloma cell line that has lost imunoglobulin expression but permits construction of antibody-secreting hybrid cell lines. *J. Immunol.* 123: 1548 (1979).

Keenan A M, Weinstein J N, Carrasquillo J A, Bunn P A, Reynolds J C, Foon K A et al. Immunolymphoscintigraphy and the dose dependence of $^{111}$In-labeled T101 monoclonal antibody in patients with cutaneous T-cell lymphoma. *Cancer Res.* 47: 6093–6099 (1987).

Köhler, G., Milstein, C. Continous culture of fused cells secreting antibody of predefined specifity. *Nature* 265: 495 (1975)

Koopman, G, Heider, K.-H., Horts, E., Adolf, G. R., van den Berg, F., Ponta, H., Herrlich, P. Pals. S. T. Activated human lymocytes and aggressive Non-Hodgkin's lymphomas express a homologue of the rat metastasis-associated variant of CD44. *J. Exp. Med* 177: 897–904 (1993).

Kreitman R J Hansen H J, Jones A L, FitzGerald D J P, Ooldenberg D M, Pastan I. Pseudomonas exotoxin-based immunotoxins containing the antibody LL2 or LL2-Fab' induce regression of subcutaneous human B-cell lymphoma in mice. *Cancer Res.* 53: 819–825 (1993).

Larson S M, Cheung N-K V, Leibel S A. Radioisotope Conjugates. In: DeVita V T, Hellman S, Rosenberg S A (Eds.). *Biological therapy of cancer*. J. B. Lippincott Comp., Philadelphia, 496–511(1991).

Lenhard R E, Order S E, Spunberg J J, Asbell S O, Leibel S A. Isotopic immunoglobulin. A new systemic therapy for advanced Hodgkin's Disease. *J. Clin. Oncol.* 3: 1296–1300 (1985).

Lesley J, Hyman R, Kincade P W. CD44 and its interaction with extracellular matrix. *Adv. Immunol.* 54: 271–335 (1993)

Mackay C R, Terpe H J, Stauder R, Marston W L, Stark H, Günthert U. Expression and modulation of CD44 variant isoforms in humans. *J. Cell. Biol.* 124 (1–2): 71–82 (1994).

Möller P, Eichelmann A, Mechtersheimer G, Koretz K. Expression of beta 1-integrins, H-CAM (CD44) and LECAM-1 in primary gastrointestinal B-cell lymphomas as compared to the adhesion receptor profile of the gut-associated lymphoid system, tonsil and peripheral lymph node. *Int. J. Cancer* 49 (6): 846–855 (1991).

Möller P, Eichelmann A, Leithauser F, Mechtersheimer G, Otto H F. Venular endothelium binding molecules CD44 and LECAM-1 in normal and malignant B-cell populations. A comparative study. *Virchows Arch.* (A) 421 (4): 305–313 (1992).

Mulder J W R, Kruyt P H M, Sewnath M, Oosting J, Seldenrijk C A, Weidema W F, Offerhaus G J, Pals S T. Expression of exon v6 containing CD44 proteins in human colorectal cancer is associated with unfavorable prognosis in long term follow up. *Lancet* 344: 1470–1472 (1994).

Mulshine J L, Magnani J L, Linnoila R I: Applications of monoclonal antibodies in the treatment of solid tumors. In: DeVita V T, Hellman S, Rosenberg S A (Eds.). *Biological therapy of cancer*. J. B. Lippincott Comp., Philadelphia, 563–588 (1991).

Nesbit M, Fu Z F, McDonald-Smith J, Steplewski Z, Curtis P J. Production of a functional monoclonal antibody recognizing human colorectal carcinoma cells from a baculovirus expression system. *J. Immunol. Methods* 151: 201–208 (1992).

Pals S T, Horst E, Ossekoppele G J, Figdor C G, Scheper R J, Meijer C J. Expression of lymphocyte homing receptor as a mechanism of dissemination in non-Hodgkin's lymphoma. *Blood* 73 (4): 885–888 (1989).

Pals S T, Koopman G, Griffioen A, et al. A variety of isoforms with functions in cell adhesion and tumor metastasis, in Shimiziu (Ed.): Lymphocyte adhesion molecules, Austin, Texas, R. G. *Landes Comp.*, 1993, p 135.

Perkins A C, Pimm M V. A role for gamma scintigraphy in cancer immunology and immunotherapy. *Eur. J. Nucl. Med* 19: 1054–1063 (1992).

Picker L J, Medeiros L J, Weiss L M, Warnke R A, Butcher E C. Expression of lymphocyte homing receptor antigen in non-Hodgkin's lymphoma. *Am. J. Pathol.* 130 (3): 496–504 (1988).

Press O W, Eary J F, Badger C C, Martin P J, Appelbaum F R, Levy R, Miller R, Brown S, Nelp W B, Krohn K A, Fisher D, DeSantes K, Porter B, Kidd P, Thomas E D, Bernstein I D. Treatment of refractory Non-Hodgkin's lymphoma with radiolabeled MB-1 (anti-CD37) antibody. *J. Clin. Oncol.* 7: 1027–1038 (1989).

Press O W, Eary J F, Appelbaum F R, Martin P J, Nelp W B Glenn S, Fisher D J, Porter B, Metthews D C Gooley T, Bernstein I D. Phase II trial of $^{131}$I-B1 (anti-CD20) antibody therapy with autologous stem cell transplantation for relapsed B cell lymphomas. *Lancet* 346: 336–340 (1995).

Quadri S M, Vriesendorp H M, Leichner P K, Williams J R. Evaluation of indium- 111 and yttrium-90 labeled linker immunoconjugates in nude mice and dogs. *J. Nucl. Med* 34: 938–945 (1993).

Ristamaki R, Joensuu H, Salmi M, Jalkanen S. Serum CD44 in malignant lymphoma: an association with treatment response. *Blood* 84 (1): 238–243 (1994).

Ristamaki R, Joensuu H, Soderstrom K O, Jalkanen S. CD44v6 expression in non-Hodgkin's lymphoma: an association with low histological grade and poor prognosis. *J. Pathol.* 176 (3): 259–267 (1995).

Rudy W, Hofmann M, Schwartz-Albiez R, Zoller M, Heider K H, Ponta H, Herrlich P. The two major CD44 proteins expressed on a metastatic rat tumor cell line are derived from different splice variants: each one individually suffices to confer metastatic behavior. *Cancer Res.* 53 (6): 1262–1268 (1993).

Salles G, Zain M, Jiang W M, Boussiotis V A, Shipp M A. Alternatively spliced CD44 transcripts in diffuse large-cell lymphomas: characterization and comparison with normal activated B cells and epithelial malignancies. *Blood* 82 (12): 3539–3547 (1993).

Sambrook, J., Fritsch E. E., Maniatis I., Molecular cloning. Cold Spring Harbor Laboratory Press, Cold Spring Harbor (1989).

Schrappe M, Bumol T F, Apelgren L D, Briggs S L, Koppel G A, Markowitz D D, Mueller B M, Reisfeld R A. Long-term growth suppression of human glioma xenografts by chemoimmunoconjugates of 4-desacetylvinblastine-3- carboxyhydrazide and monoclonal antibody 9.2.27. *Cancer Res.* 52: 3838–3844 (1992).

Screaton, G. R., Bell, M. V., Jackson, D. G., Cornelis, F. B., Gerth, U., and Bell, J. I. Genomic structure of DNA encoding the lymphocyte homing receptor CD44 reveals at least 12 alternatively spliced exons. *Proc. Natl. Acad Sci. U.S.A.* 89: 12160–12164 (1992).

Sears H F, Mattis J, Herlyn D, Hayry P, Atkinson B, Ernst C, Steplewski Z, Koprowski H. Phase-I clinical trial of monoclonal antibody in treatment of gastrointestinal tumours. Lancet 1982 (1): 762–765 (1982).

Seiter, S, Arch, R., Reber, S., Komitowski, D., Hofmann, M., Ponta, H:, Herrlich, P., Matzku, S., Zöller, M. Prevention of tumor metastasis formation by anti-variant CD44. *J. Exp. Med.* 177: 443–455 (1993).

Senter P D, Schreiber G J, Hirschberg D L, Ashe S A, Hellström K E, Hellström I. Enhancement of the in vitro and in vivo antitumor activities of phosphorylated mitomycin C and etoposide derivatives by monoclonal antibody-alkaline phosphatase conjugates. *Cancer Res.* 49: 5789–5792 (1989).

Shin S–U, Morrison S L. Production and properties of chimeric antibody molecules. *Methods Enzymol.* 178: 459–476 (1989).

Siccardi A G, Buraggi G L, Callegaro L, Colella A C, DeFilippi P G et al. Immunoscintigraphy of adenocarcinomas by means of radiolabeled F(ab')$_2$ fragments of an anti-carcinoembryonic antigen monoclonal antibody: a multicenter study. *Cancer Res.* 49: 3095–3103 (1989).

Smith, D B., Johnson, K. S. Single-step purification of polypeptides expressed in *Escherchia coli* as fusions with glutathione S-transferase. Gene 67: 31 (1988).

Srivastava S C (Ed.). Radiolabeled monoclonal antibodies for imaging and therapy. *Life Sciences Series* A 152, Plenum New York (1988).

Stamenkovic I, Amiot M, Pesando J M, Seed B. A lymphocyte molecule implicated in lymph node homing is a member of the cartilage link protein family. *Cell* 56 (6): 1057–1062 (1989).

Stauder R, Eisterer W, Thaler J, Günthert U. CD44 variant isoforms in non-Hodgkin's lymphoma: a new independent prognostic factor. *Blood* 85 (10): 2885–2899 (1995).

Tanabe K K, Ellis L M, Saya H. Expression of CD44R1 adhesion molecule in colon carcinomas and metastases. *Lancet* 341 (8847): 725–726 (1993).

Terpe H J, Stark H, Prehm P, Ganthert U. CD44 variant isoforms are preferentially expressed in basal epithelial of non-malignant human fetal and adult tissues. *Histochemistry* 101(2): 79–89 (1994).

Theuer C P, Kreitman R J, FitzGerald D J, Pastan I. Immunotoxins made with a recombinant form of pseudomonas exotoxin A that do not require proteolysis for activity. *Cancer Res.* 53: 340–347 (1993).

Thomas, G D., Dykes, P. W., Bradwell, A. R. Antibodies for tumour immunodetection and methods for antibody radiolabeling. In: Catty, D. (Ed.). *Antibodies Vol.* II. IRL Press Oxford, 223–244 (1989).

Thompson C H, Stacker S A, Salehi N, Lichtenstein M, Leyden M J, Andrews J T. Immunoscintigraphy for detection of lymph node metastases from breast cancer. *Lancet* 1984 (2): 1245–1247 (1984).

Tölg, C., Hofmann, M., Herrlich, P., and Ponta, H. Splicing choice from ten variant exons establishes CD44 variability. *Nucleic Acids. Res.* 21: 1225–1229 (1993).

Vitetta E S, Thorpe P E. Immunotoxins. In: DeVita V T, Hellman S, Rosenberg S A (Eds.). *Biological therapy of cancer.* J. B Lippincott Comp., Philadelphia, 482–495 (1991).

Vitetta E S, Stone M, Amlot P, Fay J, May R, Till M, Newman J, Clark P, Collins R, Cunningham D, Ghetie V, Uhr J W, Thorpe P E. Phase I immunotoxin trial in patients with B-cell lymphoma. *Cancer Res.* 51: 4052–4058 (1991).

Vriesendorp H M, Herbst J M, Germack M A, Klein J L, Leichner P K, Loudenslager D M, Order S E. Phase I–II studies of yttrium-labeled antiferritin treatment for end stage Hodgkin's diesease, including Radiation Therapy Oncology Group 87–01. *J. Clin Oncol.* 9: 918–928 (1991).

Vriesendorp H M, Morton J D, Quadri S M. Review of five consecutive studies of radio-labeled immunoglobulin therapy in Hodgkins's Disease. *Cancer Res.* (Suppl.) 55: 5888s-5892s (1995).

Wang S-M, Chern J-W, Yeh M-Y, Ng J C, Tung E, Roffler S R. Specific activation of glucuronide prodrugs by antibody-targeted enzyme conjugates for cancer therapy. *Cancer Res.* 52: 4484–4491 (1992).

Weiner L M, O'Dwyer J, Kitson J, Comis R L, Frankel A E, Bauer R J, Kopnrad M S, Groves E S. Phase I evaluation of an anti-breast carcinoma monoclonal antibody 260F9-recombinant ricin A chain immunoconjugate. *Cancer Res.* 49: 4062–4067 (1989).

Weiner L M, Holmes M, Adams G P, LaCreta V, Watts P, Garcia de Palazzo I. A human tumor xenograft model of therapy with a bispecific monoclonal antibody targeting c-erbB-2 and CD16. *Cancer Res.* 53 (1): 94–100 (1993).

Weiner L M, Holmes M, Richeson A, Godwin A, Adams G P Hsieh-Ma S T, Ring D B, Alpaugh R K. Binding and cytotoxicity characteristics of the bispecific murine monoclonal antibody 2B1. *J. Immunol.* 151 (5): 2877–2886 (1993).

Wilbur, D S., Hadley, S. W., Hylarides, M D., Abrams, P. G., Beaumier, P. A., Morgan, A. C., Reno, J. M., Fritzberg, A R. Development of a stable radioiodinating agent to label monoclonal antibodies for radiotherapy of cancer. *J. Nucl. Med.* 30: 216–226 (1989).

Winter, G., Griffith, A. D., Hawkins, R. E., Hoogenboom, H. R. Making antibodies by phage display technology. *Ann. Rev. Immunol.* 12, 433–455 (1994).

What is claimed is:

1. A method of diagnosing Hodgkin's lymphomas, comprising detecting the expression of the variable exon v10 in the CD44 gene in a patient or in a sample obtained from a patient, wherein the expression of the variable exon v10 in the CD44 gene indicates Hodgkin's lymphomas.

2. The method of claim 1, comprising detecting an antibody molecule bound to an epitope within the amino acid sequence coded by the variable exon v10 of the CD44 gene.

3. The method of claim 2, wherein amino acid sequence is SEQ ID NO:2.

4. The method of claim 2, wherein the antibody molecule is selected from the group consisting of: a monoclonal antibody, a Fab-fragment of an immunoglobulin, a F(ab')$_2$-fragment of an immunoglobulin and a recombinantly produced antibody.

5. The method of claim 4, wherein the recombinantly produced antibody is selected from the group consisting of: a recombinantly produced chimeric antibody, recombinantly produced humanized antibody and recombinantly produced single chain antibody (scFv).

6. The method of claim 2, wherein the antibody molecule is linked to a radioactive isotope, radioactive compound, enzyme, toxin, cytostatic, prodrug or immunomodulatory polypeptide.

7. The method of claim 6 wherein the immunomodulatory polypeptide is a cytokine.

* * * * *